(12) United States Patent
Jennewein et al.

(10) Patent No.: US 12,157,754 B2
(45) Date of Patent: Dec. 3, 2024

(54) SIMPLE METHOD FOR THE PURIFICATION OF LACTO-N-NEOTETRAOSE (LNNT) FROM CARBOHYDRATES OBTAINED BY MICROBIAL FERMENTATION

(71) Applicant: Chr. Hansen HMO GmbH, Rheinbreitbach (DE)

(72) Inventors: Stefan Jennewein, Bad Honnef (DE); Markus Helfrich, Bad Hoenningen (DE)

(73) Assignee: Chr. Hansen HMO GmbH, Rheinbreitbach (DE)

(*) Notice: Subject to any disclaimer, the term of this patent is extended or adjusted under 35 U.S.C. 154(b) by 0 days.

(21) Appl. No.: 18/195,502

(22) Filed: May 10, 2023

(65) Prior Publication Data
US 2023/0271992 A1 Aug. 31, 2023

Related U.S. Application Data

(62) Division of application No. 17/053,317, filed as application No. PCT/EP2019/061530 on May 6, 2019, now Pat. No. 11,685,758.

(30) Foreign Application Priority Data

May 7, 2018 (EP) .................... 18171114

(51) Int. Cl.
C07H 1/08 (2006.01)
C07H 3/06 (2006.01)
C12N 9/10 (2006.01)

(52) U.S. Cl.
CPC ............... *C07H 1/08* (2013.01); *C07H 3/06* (2013.01); *C12N 9/1051* (2013.01)

(58) Field of Classification Search
CPC .......... C07H 1/08; C07H 3/06; C12N 9/1051
USPC .................................................... 536/25.41
See application file for complete search history.

(56) References Cited

U.S. PATENT DOCUMENTS

| | | | |
|---|---|---|---|
| 10,435,427 B2 | 10/2019 | Jennewein et al. | |
| 2016/0237104 A1 | 8/2016 | Jennewein et al. | |
| 2018/0305724 A1 | 10/2018 | Jennewein et al. | |
| 2019/0292211 A1 | 9/2019 | Jennewein et al. | |
| 2021/0230199 A1 | 7/2021 | Jennewein et al. | |

FOREIGN PATENT DOCUMENTS

| | | | |
|---|---|---|---|
| EP | 3141610 A1 | 3/2017 | |
| JP | 2008506949 A | 3/2008 | |
| JP | 2016530888 A | 10/2016 | |
| WO | 9815581 A1 | 4/1998 | |
| WO | 2001004341 A1 | 1/2001 | |
| WO | 2006017171 A2 | 2/2006 | |
| WO | 2007056191 A2 | 5/2007 | |
| WO | 2015036138 A1 | 3/2015 | |
| WO | 2015049331 A1 | 4/2015 | |
| WO | 2015106943 A1 | 7/2015 | |
| WO | 2017182965 A1 | 10/2017 | |
| WO | WO 2017/182965 | * 10/2017 | |
| WO | 2019003133 A1 | 1/2019 | |

OTHER PUBLICATIONS

Miwa et al. Cooperation of β-galactosidase and β-N-acetylhexosaminidase from bifidobacteria in assimilation of human milk oligosaccharides with type 2 structure. Glycobiology vol. 20 No. 11 pp. 1402-1409, 2010. (Year: 2010).*
Andres Cordova, et al., "Purification of galacto-oligosaccharides (GOS) by three-stage serial nanofiltration units under critical transmembrane pressure conditions," Chemical Engineering Research and Design, (2017) 117: 488-499.
Bernard Priem et al., "A new fermentation process allows large-scale production of human milk oligosaccharides by metabolically engineered bacteria," Glycobiology, (2002), 12(4): 235-240.
Chandrapala et al., "Removal of lactate from acid whey using nanofiltration," J Food Engineering, 2016, 177:59-64.
Claire Dumon et al., "In vivo fucosylation of lacto-N-neotetraose and lacto-N-neohexaose by heterologous expression of Helicobacter pylori a-1, 3 fucosyltransferase in engineered *Escherichia coli*," Glycoconjugate journal, (2001) 18(6):465-474.
Douglas B. Sarney et al., "A novel approach to the recovery of biologically active oligosaccharides from milk using a combination of enzymatic treatment and nanofiltration," Biotechnology and Bioengineering, (2000), 69(4):461-467.
Florian Baumgartner et al., "Synthesis of the human milk oligosaccharide lacto-N-tetraose in metabolically engineered, plasmid-free *E. coli*," ChemBioChem, (2014), 15(13): 1896-1900.
International Search Report for Application No. PCT/EP2019/061530 mailed Nov. 9, 2019.
Karina Altmann et al., "Comparison of the efficiency of different NF membranes for the enrichment of milk Oligosaccharides from bovine milk," European Food Research and Technology, (2015), vol. 241, No. 6: 803-815.
Lars Bode et al., "Making human milk oligosaccharides available for research and application—approaches, challenges, and future opportunities," Prebiotics and probiotics in human milk: origins and functions of milk-borne oligosaccharides and bacteria, (2016), Chapter 9: 251-295.
Lars Bode, et al., "Potential public health impact of human milk oligosaccharides," Prebiotics and probiotics in human milk, (2016), Chapter 7: 207-222.
Luo et al., "An integrated membrane system for the biocatalytic production of 3'-sialyllactose from dairy by-products," Bioresource Technology, 2014, doi: http://dx.doi.org/10.1016/j.biortech.2014.05.003, 26 pages.

(Continued)

*Primary Examiner* — Yih-Horng Shiao (57) ABSTRACT

Provided is a method for the purification of lacto-N-neotetraose from other carbohydrates, characterized in that the method comprises the steps of subjecting an aqueous solution containing lacto-N-neotetraose to two membrane filtration steps using different membranes or of subjecting an aqueous solution containing lacto-N-neotetraose to a membrane filtration step and a continuous chromatography.

11 Claims, 3 Drawing Sheets

(56) References Cited

OTHER PUBLICATIONS

Miwa et al., "Cooperation of β-galactosidase and β-N-acetylhexosaminidase from bifidobacteria in assimilation of human milk oligosaccharides with type 2 structure," Glycobiology, 2010, 20(11):1402-1409.
Usashima T. et al., (2011) Milk Oligosaccharides, Nova Biomedical Books, New York ISBN 978-1-61122-831-1.

* cited by examiner

SIMPLE METHOD FOR THE PURIFICATION OF LACTO-N-NEOTETRAOSE (LNNT) FROM CARBOHYDRATES OBTAINED BY MICROBIAL FERMENTATION

CROSS-REFERENCE TO RELATED APPLICATIONS

This application is a divisional of U.S. Patent Application No. 17/053,317, filed Nov. 5, 2020, which is the National Stage entry of International Application No. PCT/EP2019/061530, filed May 6, 2019, which claims priority to European Patent Application No. 18171114.4, filed May 7, 2018. The entire contents of these priority applications are incorporated herein by reference.

FIELD OF THE INVENTION

The present invention relates to processes for the purification of lacto-N-neotetraose (Gal($\beta$-1-4)GlcNAc($\beta$1-3)Gal ($\beta$1-4)Glc). More specifically, the present invention concerns a simple and economical process for separating lacto-N-neotetraose from other carbohydrates such as lacto-N-trioses, lactose and monosaccharides as well as larger oligosaccharides, such as para-lacto-N-neohexaose which may be present as contaminating carbohydrates in a fermentation broth if said lacto-N-neotetraose is produced by microbial fermentation.

DESCRIPTION OF RELATED ART

Human milk is regarded as the best diet for the development of an infant. It is composed of fats, proteins, vitamins, minerals, trace elements and complex oligosaccharides. Besides lactose, human milk—as well as milk of other mammals—contains various structurally diverse oligosaccharides which are also known as human milk oligosaccharides (HMOs) (Urashima T. et al., (2011) Milk Oligosaccharides, Nova Biomedical Books, New York ISBN 978-1-61122-831-1).

Efforts to produce HMOs chemically or by biotechnologically based approaches attracted attention due to the beneficial properties of HMOs on the development of the gastrointestinal flora, thus advocating their use in nutritional products (in particular infant and toddler nutrition, but also medical and adult nutrition products).

Besides these probiotic properties, many other positive effects of HMOs were observed so far, expanding their field of application (Morrow A. L. & Yu, Y. (2016) Potential public health impact of human milk oligosaccharides. In: Prebiotics and probiotics in human milk. McGuire, M., McGuire, M. & Bode, L. (Eds.) Academic Press, London, pp 207-222).

The limited supply and difficulties of obtaining pure factions of individual human milk oligosaccharides lead to the development of chemical routes to produce some of these complex molecules. However, synthesis of human milk oligosaccharides by chemical synthesis, by enzymatic synthesis or by fermentation proved to be challenging. At least production of large-scale quantities as well as quantities sufficient for food applications proved difficult until today.

Due to the challenges involved in the chemical synthesis of human milk oligosaccharides, several enzymatic methods and fermentative approaches were developed. In particular the fermentative approach requires purification of the desired oligosaccharide from a highly complex fermentation broth containing several hundreds of different molecules. The carbohydrate fraction of the fermentation broth alone is composed of a complex mixture of mono- and oligosaccharides including substrates (e.g. lactose, and other sugars used as carbon source), biosynthetic intermediates, individual monosaccharides, metabolic side products and other polysaccharides synthesized by the microbe. Moreover, the structures of many of the oligosaccharides occurring in the fermentation broth are structurally unknown (e.g. oligosaccharides produced by the synthesizing host naturally like cell surface glycosylation structures). Thus, in many cases the purification of a biotechnological product is much more expensive than its production by fermentation. In particular the fermentation of lacto-N-neotetraose is often associated with an excessive synthesis of lacto-N-triose II, a biosynthetic intermediate in the biosynthesis of lacto-N-neotetraose, which is often exported from the cell into the medium. Lacto-N-triose II can be removed from the fermentation broth by a glycosidase treatment or a chromatographic step in the purification process. Due to the $\beta$-1,4-linked galactose residue at the non-reducing end of lacto-N-neotetraose the non-reducing end closely resembles lactose, which often leads a further glycosylation reaction by glycosyltransferases present in the microbial fermentation strain of by the glycosyltransferases used in the biocatalytic reaction. This leads to the formation of pentaoses, hexaoses, heptaoses and even larger oligosaccharides (overglycosylation of the desired lacto-N-neotetraose product). In addition, autoclaving (heat treatment) of carbohydrates (for example lactose) leads to the formation of undesired by-products such as aldol or mayard products, or rearrangement reactions (e.g. conversion of lactose to lactulose). Presence of such contaminants, in particular in larger amounts, in the final product is unwanted or unacceptable.

"State of the art" processes for purifying individual oligosaccharides from a fermentation broth are technically complex and often uneconomical, in particular when said oligosaccharide is intended for food applications. For the purification of the disaccharide lactose or sucrose from complex mixtures such as whey or molasses, industrial scale processes have been developed which involve multiple crystallization steps. However, said methods are elaborate and only lead to low yields. Also, these processes are not applicable for rendering a saccharide suitable for use in the food industry, because whey and molasses are food product already.

However, filtration processes like ultrafiltration microfiltration and nanofiltration are technically easy to perform, if all process parameters are known and optimized. Diafiltration is another suitable process that involves the addition of fresh water to a solution in order to remove membrane permeable components. Ultrafiltration and microfiltration are usually used for separating much larger molecules like proteins or cells from a fermentation broth or a aqueous solution. Additionally, the removal of water, minerals and very small molecules by nanofiltration is well known and used in dairy industry for the concentration and demineralization of whey. In most cases membrane materials for nano- and ultrafiltration base on materials like piperazine, polyamide, polyethersulfone, polyethylene glycol and ceramic. Membranes can be assembled e.g. as hollow fiber modules, spiral wound modules and flat sheet membranes and the assembly can lead to different separation performances. In general, nanofiltration membranes possess a molecular weight cut-off in the range of 150-300 Daltons. Membranes with a molecular weight cut-off in the range of 400-600 Daltons are very rare, especially for the large-scale industrial production. This makes the separation of oligosaccharides still complex because other separation techniques like a chromatography, either batch-wise or continuously, are necessary.

For the production of human milk oligosaccharides by microbial fermentation, recombinant microorganisms (recombinant bacterial or yeast strains) are used. Such use results in the contamination of the fermentation broth with recombinant material such as nucleic acid molecules or polypeptides resulting from the microorganism. However, contamination of a product for human consumption with recombinant DNA or proteins is neither acceptable by regulatory authorities nor by consumers today. Thus, any nucleic acids and proteins resulting from the recombinant microorganism need to be removed from the desired human milk oligosaccharide. Detection limits for recombinant DNA molecules are very low today which requires thorough purification schemes. In case of qPCR based detection of DNA, even as little as a single DNA molecule can be detected in a sample.

Chromatographic processes for the purification of lacto-N-neotetraose and the closely related human milk oligosaccharide lacto-N-tetraose (Galβ1-3GlcNAcβ1-3-Gal(β1-4Glu) were employed, in particular gel filtration chromatography. (Dumon et al., (2001) In Vivo Fucosylation of lacto-N-neotetraose and lacto-N-neohexaose by Heterologous Expression of Helicobacter pylori α1,3-Fucosyltransferase in Engineered *Escherichia coli*. Glycoconj. J. 18, 465-474; Priem et al., (2002) A new fermentation process allows large-scale production of human milk oligosaccharides by metabolically engineered bacteria. Glycobiology 12, 235-240; Baumgärtner et al (2014) Synthesis of the human milk oligosaccharide lacto-N-tetraose in metabolically engineered, plasmid-free *E. coli*. Chembiochem 15, 1896-1900). Whereas gel filtration chromatography is a convenient lab scale method only simulated moving bed chromatography represents a suitable method for purification of LNnT at scales compatible to food production. However, all other published processes suffer from the problem that contaminating carbohydrates, in particular the ones related to the overglycosylation, cannot be effectively removed from the desired product.

It was therefore an object of the present invention to provide a simple and cost efficient method for the purification of lacto-N-neotetraose from microbial fermentations, wherein nucleic acids and polypeptides originating from the recombinant microorganism can be removed from the desired oligosaccharide as well as said other carbohydrates.

Several fermentative approaches were already developed for the structural simpler HMOs such as lacto-N-neotetraose using engineered microbes such as *Escherichia coli* strains (e.g. EP 3 141 610 A1; WO 2001/004341 A1; Bode, L. et al., (2017) Making human milk oligosaccharides available for research and application—approaches, challenges, and future opportunities. In: Prebiotics and probiotics in human milk. McGuire, M., McGuire, M. & Bode, L. (Eds.) Academic Press, London, pp 251-293).

However, also other microbial fermentation approaches can be used for the production of oligosaccharides. Besides bacterial systems eukaryotic production strains can also be employed, for example yeast and in particular *Saccharomyces cerevisiae* or any close relative. In contrast to many other putative production organisms *Saccharomyces cerevisiae* is a microorganism approved for food production.

In essence, the microorganism has to be genetically engineered for lactose up-take, or for an endogenous lactose biosynthesis from a readily available carbon source (e.g. glucose, galactose, sucrose, fructose, xylose, glycerol etc.). Activities regarding lactose metabolism and side product formation should be inactivated or reduced to an extent that lacto-N-neotetraose production can be achieved. Lacto-N-neotetraose is then synthesized by the enzymatic activity of two glycosyltransferases, a β-1,3-N-acetylglucosaminyltransferase and a β-1,4-galactosyltransferase. Several glycosyltransferases for the synthesis of lacto-N-neotetraose are known such the β-1,3-N-acetylglucosaminyl transferase of *N. meningitidis* encoded by the IgtA gene and the β-1,4-galactosyl transferase of *Helicobacter pylori* encoded by the galT gene. Preferably an exporter is expressed in the recombinant microorganism for the export of the desired oligosaccharide into the fermentation medium from where said oligosaccharide may then be purified.

SUMMARY

Provided is a method for the purification of lacto-N-neotetraose which is simple, cost-efficient and scalable. The method for the purification of lacto-N-neotetraose can be performed without the use of an organic solvent for crystallization of said lacto-N-neotetraose. In addition, the method for the purification of lacto-N-neotetraose can be performed without a discontinuous chromatographic step.

Lacto-N-neotetraose (Gal(β-4)GlcNAc(β1-3)Gal(β1-4)Glc) represents a human milk oligosaccharide which inclusion into infant formula and medical food is highly desirable. The high cost of lacto-N-neotetraose prevents its widespread use in particular in infant formula. In particular, the purification of products from microbial fermentation are often elaborate and expensive. Also the use of organic solvents and discontinuous chromatographic steps make lacto-N-neotetraose and other neutral oligosaccharides prohibitively expensive. Also the use of ethanol is not acceptable by certain religious food standards, for example Halal. Thus the inventions relates to a simple cost effective method to purify lacto-N-neotetraose from microbial fermentation using an recombinant processing aid, yielding a lacto-N-neotetraose product suitable for human consumption, in particular suitable for infant food and medical nutrition products.

The purification process is based on membranes for the purification/separation of lacto-N-neotetraose (Gal(β-4)GlcNAc(β1-3)Gal(β1-4)Glc) from contaminating carbohydrates. The developed methods represents a cost efficient alternative to chromatographic or crystallisation based purification methods. The made invention is particularly relevant for the purification of lacto-N-neo-tetraose obtained by microbial fermentation using bacterial or yeasts as production hosts and biocatalysis processes using crude or purified enzymes. The method for the purification of lacto-N-neotetraose comprises two steps of membrane filtration, wherein one membrane has a molecular weight cut-off of between about 300 and about 500 Dalton, and wherein the other membrane has a molecular weight cut-off of between about 600 to about 800 Dalton.

In an aspect of the invention, either one of the two membrane filtration steps can be replaced by a step of continuous chromatography, such as simulated bed chromatography (SMB).

DETAILED DESCRIPTION

Provided is a method for the purification of lacto-N-neotetraose from other carbohydrates, wherein the method comprises the steps of subjecting an aqueous solution containing lacto-N-neotetraose and said other carbohydrates to two membrane filtration steps using different membranes, wherein one membrane has a molecular weight cut-off of between about 300 to about 500 Dalton, and wherein the other membrane as a molecular weight cut-off of between about 600 to about 800 Dalton.

The membrane having a molecular weight cut-off of between about 300 to about 500 Dalton allows removal of the bulk of carbohydrates having a molecular weight that is smaller than that of LNnT. Upon filtration, LNnT and carbohydrates having a molecular weight larger than that of LNnT are retained in the retentate.

In an additional and/or alternative embodiment, the membrane having a molecular weight cut-off of between about 300 to about 500 Dalton has a pore size of 1 to 2 5 nm.

Suitable membranes for removal of the bulk of carbohydrates having a molecular weight that is smaller than that of LNnT are—for example—TriSep XN-45 (TriSep Corporation, USA), Dairy DK (Suez Water Technologies, formerly GE) and Filmtech NF270 (Dow, Midland, MI, USA).

The membrane having a molecular weight cut-off of between about 600 to about 800 Dalton possesses permeability for lacto-N-neotetraose and carbohydrates having a molecular weight smaller than that of LNnT. Upon filtration, LNnT is present in the filtrate whereas carbohydrates having a molecular weight larger than that of LNnT remain in the retentate.

In an additional and/or alternative embodiment, the membrane having a molecular weight cut-off of between about 600 to about 800 Dalton has a pore size of 2.5 to 3 nm.

Suitable membranes for possessing permeability for LNnT and retaining whereas carbohydrates having a molecular weight larger than that of LNnT in the retentate are—for example—TangenX SIUS TFF 0.65kDa membrane (Repligen Corporation), Zirkonia modules 3 nm (Pervatech BV) and S-CUT YSNF-YS600 (CUT/Bürkert).

The method circumvents the use of expensive discontinuous chromatographic steps and also renders precipitation or crystallisation steps using organic solvents unnecessary. Thus, in an additional and/or alternative embodiment, the method does not comprise one or more discontinuous chromatography steps and/or one or more steps of precipitating and/or crystallizing LNnT by using an organic solvent.

In an additional and/or alternative embodiment of the method, either one of the two membrane filtration steps can be replaced with a continuous chromatography such as an simulated moving bed (SMB) chromatography.

In an additional and/or alternative embodiment, the method for the purification of lacto-N-neotetraose from other carbohydrates is characterized in that the method comprises the steps of subjecting an aqueous solution containing lacto-N-neotetraose to a membrane filtration step using a membrane having a molecular weight cut-off of between about 300 to about 500 Dalton, and subjecting the aqueous solution to a continuous chromatography to remove carbohydrates having a molecular weight larger than that of LNnT from the aqueous solution.

Preferably, the membrane filtration step is performed prior to the continuous chromatograph in that the retentate of the membrane filtration step is subjected to the continuous chromatography.

In another additional and/or alternative embodiment, the method for the purification of lacto-N-neotetraose from other carbohydrates is characterized in that the method comprises the steps of subjecting an aqueous solution containing lacto-N-neotetraose to a membrane filtration step using a membrane having a molecular weight cut-off of between about 600 to about 800 Dalton, and subjecting the aqueous solution to a continuous chromatography to remove carbohydrates having a molecular weight smaller than that of LNnT from the aqueous solution.

Preferably, the continuous chromatography is performed prior to the membrane filtration step in that the eluate of the continuous chromatography is subjected to the membrane filtration step.

In an additional and/or alternative embodiment, the aqueous solution is obtained from a fermentation or enzymatic process for the production of lacto-N-neotetraose.

The method described herein is suitable for the purification of the human milk oligosaccharide lacto-N-neotetraose from a microbial fermentation or biocatalysis reaction in multi-ton amounts, because it is economically feasible and scalable.

In an additional and/or alternative embodiment, the aqueous solution is obtained from a fermentation by separating the biomass from the fermentation broth. Preferably, separating the biomass from the fermentation broth comprises at least one step of ultrafiltration, preferably two steps of ultrafiltration, more preferably a first ultrafiltration using a membrane having a molecular weight cut-off of about 500 kDa and a second ultrafiltration using a membrane having a molecular weight cut-off of about 150 kDa.

In an additional and/or alternative embodiment, the aqueous solution is treated with a cation exchange resin, preferably in $H^+$ form, and an anion exchange resin, preferably in $Cl^-$ form, more preferably before subjecting the aqueous solution to the membrane filtration steps.

In an additional and/or alternative embodiment, the method further comprises a step of dialysis, preferably a step of electrodialysis, for removal of ions.

The product can be most conveniently supplied as a sterile concentrate or as a spray-dried product.

The method allows purifying lacto-N-neotetraose, i.e. separating LNnT from other carbohydrates, wherein the purity of lacto-N-neotetraose in the aqueous solution is ≤70%, ≤60%, ≤50%, ≤40%, ≤30%, ≤20%; ≤10% or ≤5% prior to the purification and/or the aqueous solution contains lacto-N-neotetraose at a purity of ≥80%, preferably of ≥85% or more preferably ≥90% after the purification.

In an additional and/or alternative embodiment, the purification comprises the following steps:
i.) separating the biomass from the fermentation broth;
ii.) subjecting the cell-free fermentation broth to ion-exchange resin treatment for the removal of charged material;
iii.) subjecting the aqueous solution obtained in step ii. to a membrane filtration step to remove carbohydrates having a molecular weight smaller than that of lacto-N-neotetraose;
iv.) subjecting the retentate obtained in step iii. to a membrane filtration step to remove carbohydrates having a molecular weight larger than that of lacto-N-neotetraose;
v.) increasing the concentration of the lacto-N-neotetraose present in the filtrate of step iv.

Whereas other procedures used for the purification of lacto-N-neotetraose are rather complex and therefore expensive the method described herein before relies mainly on the use of two membrane filtration steps. In one membrane filtration step contaminants smaller than the desired product lacto-N-neotetraose are filtered away. In a second filtration step, molecules larger molecules are filtered away from the desired product.

In another embodiment, one of the membrane filtration steps can be substituted by a simulated moving bed chromatography process. Simulated moving bed chromatography represents—in contrast to other chromatographic processes—a continuous chromatographic procedure, which can be also applied at multi-ton scale and is compared to other discontinuous chromatographic processes extremely cost effective.

In an additional and/or alternative embodiment, the method for the purification of LNnT comprises the steps:
i.) separating the biomass from the fermentation broth;
ii.) subjecting the cell-free fermentation broth to ion-exchange resin treatment for the removal of charged material;
iii.) subjecting the aqueous solution obtained in step ii. to a membrane filtration step to remove carbohydrates having a molecular weight smaller than that of lacto-N-neotetraose;
iv.) subjecting the retentate obtained in step iii. to a continuous chromatography to remove carbohydrates having a molecular weight larger than that of lacto-N-neotetraose; larger material from lacto-N-neotetraose;
v.) increasing the concentration of the lacto-N-neotetraose present in the eluate of step iv.

According to another embodiment of the invention, carbohydrates having a molecular weight that is smaller than that of LNnT (in particular smaller oligosaccharides and monosaccharides) can be removed by simulated moving bed chromatography and larger carbohydrates than LNnT by a membrane filtration step.

In an additional and/or alternative embodiment, the method comprises the following steps:
i.) separating the biomass from the fermentation broth;
ii.) subjecting the cell-free fermentation broth to ion-exchange resin treatment for the removal of charged material;
iii.) subjecting the aqueous solution obtained in step ii. to a continuous chromatography to remove carbohydrates having a molecular weight smaller than that of lacto-N-neotetraose;
iv.) subjecting the eluate of step iii. to a membrane filtration step to remove carbohydrates having a molecular weight larger than that of lacto-N-neotetraose;
v.) increasing the concentration of the Lacto-N-neotetraose in the filtrate obtained in step iv.

According to another embodiment of the invention one or more glycosidase are used in the method for the purification of LNnT to hydrolyze certain oligosaccharides into smaller oligosaccharides or monosaccharides. For example, the by-product lacto-N-triose II (GlcNAc(β1-3)Gal(β1-4)Glc) can be degraded into N-actylglucosamine and lactose (Gal(β1-4)Glc) by the N-acetylhexosaminidase encoded by the bbhl gene of *Bifidobacterium bifidum*. Lactose can be further degraded into the monosaccharides glucose and galactose by a β-galactosidase (for example the *Escherichia coli* β-galactosidase can be used encoded by the lacZ gene, which can be easily overexpressed). The bbhl gene of *Bifidobacterium bifidum* can also be obtained by overexpression in *E. coli*.

In an additional and/or alternative embodiment, the method comprises the steps of
i.) separating the biomass from the fermentation broth;
ii.) adding one or more glycosidases to the fermentation broth, wherein said glycosidases do not hydrolyze LNnT, such as—for example—the Bbhl the N-acetylhexosaminidase of *B. bifidum;*
iii.) subjecting the cell-free fermentation broth to ion-exchange resin treatment for the removal of charged material;
iv.) subjecting the aqueous solution obtained in step iii. to a membrane filtration step to remove carbohydrates having a molecular weight smaller than that of lacto-N-neotetraose;
v.) subjecting the retentate obtained in step iv. to a membrane filtration step to remove carbohydrates having a molecular weight larger than that of lacto-N-neotetraose;
vi.) increasing the concentration of the lacto-N-neotetraose present in the filtrate of step v.

In an additional and/or alternative embodiment, either one of the two membrane filtration steps may be substituted by a continuous chromatograph as described herein before.

In a preferred embodiment, a recombinant microorganism, more preferably a genetically engineered *E. coli,* is added to the fermentation broth at the end of the fermentation process, wherein said recombinant microorganism expresses the bbhl gene of *Bifidobacterium bifidum* and/or expresses or overexpresses a β-galactosidase, preferably the β-galactosidase encoded by the *E. coli* lacZ gene.

In an additional and/or alternative embodiment, the method comprises the following 5 steps:
i.) adding a recombinant microorganism expressing the bbhl gene of *Bifidobacterium bifidum* and/or the *E. coli* lacZ gene to the fermentation broth;
ii.) separating the biomass from the fermentation broth;
iii.) subjecting the cell-free fermentation broth to ion-exchange resin treatment for the removal of charged material;
iv.) subjecting the aqueous solution obtained in step ii. to a membrane filtration step to remove carbohydrates having a molecular weight smaller than that of lacto-N-neotetraose;
v.) subjecting the retentate obtained in step iii. to a membrane filtration step to remove carbohydrates having a molecular weight larger than that of lacto-N-neotetraose;

vi.) increasing the concentration of the lacto-N-neotetraose present in the filtrate of step iv.

In an additional and/or alternative embodiment, either one of the two membrane filtration steps may be substituted by a continuous chromatograph as described herein before.

Certain embodiments of the invention comprise one or more further optional steps, such as dialysis steps (for the removal of salts), electrodialysis (for the removal of charged molecules), activated charcoal treatment (for the decolorization of the product solution) and/or other filtration processes (like endotoxin removal and/or sterile filtration). Although not necessary, the process may comprise treatment of the aqueous solution containing LNnT with an organic solvent (such as short chain alcohols like methanol) for the precipitation of contaminating oligosaccharides or for elution after adsorption to activated charcoal with short chain alcohols and water mixtures, and/or for crystallisation of the lacto-N-neotetraose.

The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

EXAMPLES

Example 1

Fermentative Production of Lacto-N-Neotetraose

*E. coli* BL21 (DE3) was used as host for the development of strains suitable for the fermentative synthesis of LNnT. The following genes were inactivated in the host strain, lacZ (encoding the beta-galactosidase, araA (encoding the L-arabinose isomerase), wcaJ (probably encoding the UDP-glucose:undecaprenyl phosphate glucose-1phosphate transferase), wzxC (putatively encoding a colanic acid exporter, fucI (encoding the L-fucose isomerase), fucK (encoding the and L-fuculose kinase).

Engineering the LNnT production strain, additionally, the genes nagA and nagB, encoding N-acetyl-glucosamine-6-phosphate deacetylase and glucosamine-6-phosphate deaminase, respectively, were deleted. To enable LNnT production by this strain the gene lgtA from *Neisseria meningitides*, encoding a β-1,3-N-acetylglucosaminyltransferase, and lex-1, encoding the β-1,4-galactosyltransferase from *Aggregatibacter aphrophilus* were introduced in the BL21 genome by transposition. LacY from *E. coli*, encoding the lactose permease, was also chromosomally integrated. All exogenous genes are constitutively transcribed. To enhance formation of UDP-galactose as donor substrate in the galactosyltransferase reaction, the genes galE and galU, both originating from *E. coli* K12, were overexpressed by introduction of these genes under control of the promoter T5.

Besides LNnT the trisaccharide LNT II is produced by the production strain and excreted into the fermentation broth. Using *E. coli* BL21 (DE3) ΔlacZ gal+ ara-ΔwzxY-wcaJ ΔfucIK the lacZ gene and a deregulated lactose permease gene (lacY6HIS) both under the control of a constitutive promoter were introduced into the genome to construct a LNT II degradation strain. To degrade the by-product LNT-II the codon optimized gene encoding the N-acetyhexosaminidase BbhI from *Bifidobacterium bifidum* was chromosomally introduced. For faster degradation of the monosaccharide N-acetylglucosamine the genes nagA, nagB, and nagE, encoding the N-acetylglucosamine-6-phosphate deacetylase, glucosamine-6-phosphat deaminase, and PTS system N-acetylglucosamine-specific EIICBA component, respectively, originating from the host strain, were overexpressed by introduction of the nagAB operon under control of the $P_{tet}$ promoter and nagE transcribed from promoter T5. In a last step the galactose metabolism in this strain was improved by insertion of the galETKM operone from *E. coli* K12.

The production strain was cultured in a chemically defined mineral salts medium, containing 7 g/L $NH_4H_2PO_4$, 7 g/L $K_2HPO_4$, 2 g/L KOH, 0.3 g/L citric acid, 2 g/L $MgSO_4 \times 7H_2O$, and 0.015 g/L $CaCl_2 \times 6H_2O$, supplemented with 1 mL/L trace element solution (54.4 g/L ammonium ferric citrate, 9.8 g/L $MnCl_2 \times 4H_2O$, 1.6 g/L $CoCl_2 \times 6H_2O$, 1 g/L $CuCl_2 \times 2H_2O$, 1.9 g/L $H_3BO_3$, 9 g/L $ZnSO_4 \times 7H_2O$, 1.1 g/L $Na_2MoO_4 \times 2H_2O$, 1.5 g/L $Na_2SeO_3$, 1.5 g/L $NiSO_4 \times 6H_2O$), and containing glucose as carbon and energy source. Lactose was added as substrate for LNnT synthesis. Fermentation was conducted as fed-batch process; pH control was due to addition of ammonia.

A second microbial strain used for intracellular degradation of by-products was cultured in the same medium with glucose as carbon source. At the end of the LNnT production process both strains were combined in one fermentation vessel. The process was stopped when no more contaminating mono- and disaccharides and no LNT II were detected by HPLC analysis.

Example 2

Preparation of a Cell Free Fermentation Broth

The cell-mass (about 13% of the fermentation broth) was separated from the medium by ultrafiltration (0.05 μm cut-off) (CUT membrane technology, Erkrath, Germany) followed by a cross-flow filter with a MWCO of 150 kDa (Microdyn-Nadir, Wiesbaden, Germany). The cell-free fermentation broth contained 53.9% LNnT, 19.4% GlcNAc, 16.5% pLNnH, 3.9% trioses, 4.8% lactose and 1.5% disaccharides with respect to the area of the peaks of a HPLC chromatogram.

Example 3

Ion Exchange Resin Treatment of a Lacto-N-Neotetraose-Containing Cell Free Fermentation Broth The obtained cell-free fermentation broth containing 8,9 kg lacto-N-neotetraose at a purity of 29% (by dry weight) in a volume of 500 L was passed over a strong cationic ion exchanger (LEWATIT® S2568 obtained from the company Lanxess) in $H^+$ form in order to remove positive charged contaminants (size of the ion exchanger bed volume was 200 L). The elution of LNnT from the ion exchanger was continued with deionized water. The obtained solution was then set to pH 7 by the addition of sodium hydroxide solution. The solution was then (without delay) passed over an anionic ion exchanger column (bed volume of the ion exchanger was 200 L). The used strong anionic ion exchanger LEWATIT® S6368 A (Lanxess) was in the chloride ($Cl^-$) form. The elution of LNnT was continued with deionized water. The obtained solution was again neutralized to pH 7.

Example 4

First Membrane Treatment for the Removal of Smaller Molecules/Carbohydrates

The solution obtained by ion exchanger treatment was diafiltrated using a TRISEP® XN-45 (TriSep Corporation, USA) nanofiltration membrane and 800 L of deionized water. The resulting solution was further concentrated using the nanofiltration membrane (RE 8040-BE, CSM-Saehan) wherein a lacto-N-neotetraose solution with a purity of 36.2% (by dry weight) and a conductivity of 8 mS/cm was obtained.

Example 5

Second Membrane Treatment for the Removal of Larger Molecules/Carbohydrates

Figure 1:
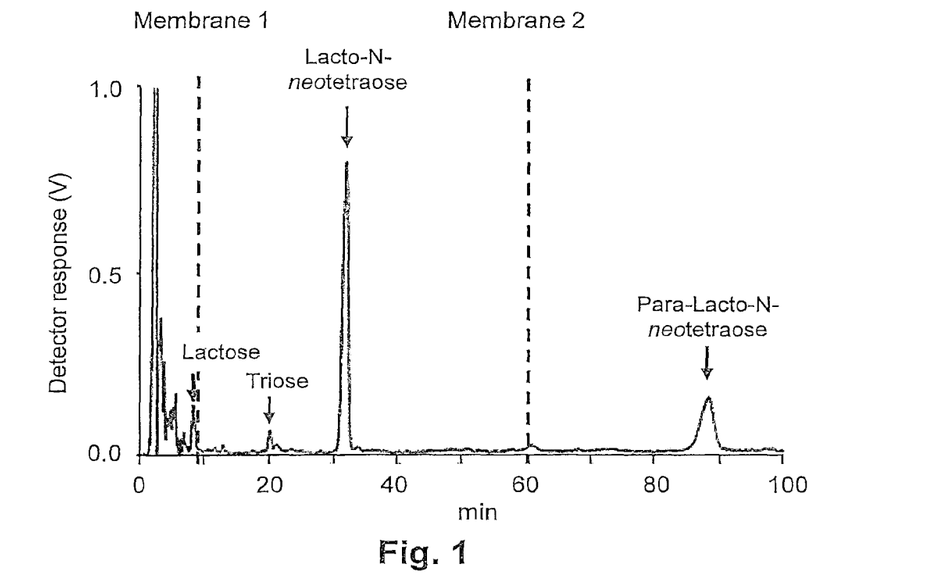
FIG. 1 displays the result of an HPLC analysis of a composition containing several saccharides and illustrates the principle for the purification of lacto-N-neotetraose using two membrane filtration steps FIG. 2 displays the result of an HPLC analysis of an eluate obtained after ion exchanger treatment of a fermentation broth after microbial fermentation for the production of lacto-N-neotetraose.
Figure 2:
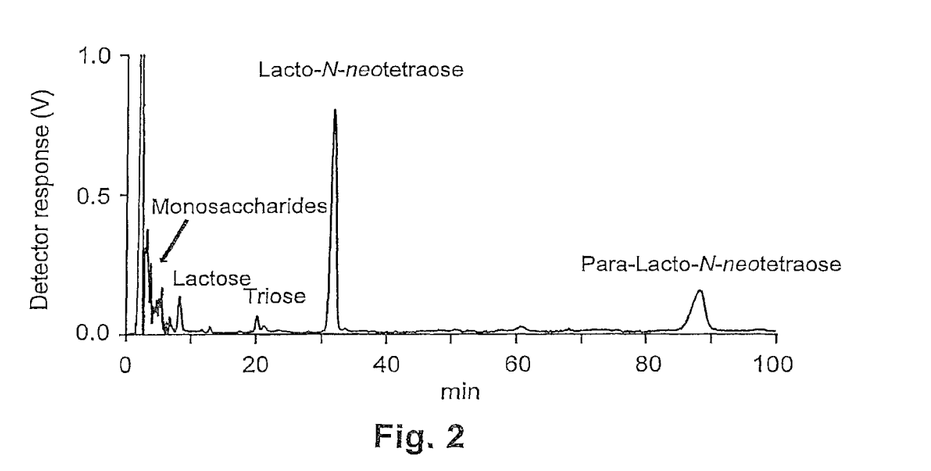
Figure 3:
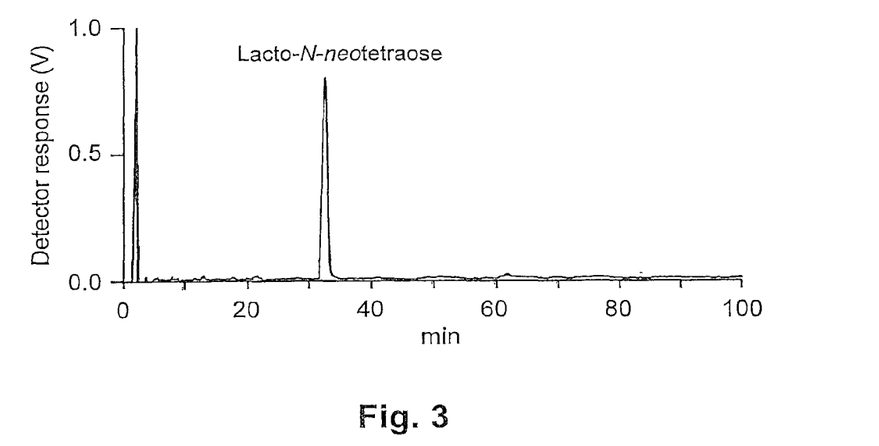
FIG. 3 displays the result of an HPLC analysis of the eluate obtained after ion exchanger treatment of a fermentation broth after microbial fermentation for the production of lacto-N-neotetraose and subjection to two membrane filtration steps.

Before second membrane treatment a solution containing lacto-N-neotetraose at a purity of 57% as determined by HPLC was obtained. For the filtration a TangenX® SIUS® TFF 0.65 kDa membrane (Repligen Corporation) was employed. In this filtration process the main fermentation by-product para-lacto-N-neohexaose was removed (FIG. 3).

Example 6

Electrodialysis Treatment

The solution was then electrodialysed to 0.4 mS/cm using a PC-Cell 15 electrodialysis apparatus (PC-Cell, Heusweiler, Germany) equipped with an PC-Cell ED 1000H membrane stack. This membrane stack was equipped with the following membranes: cation exchange membrane CEM: PK SK and the anion exchange membrane AEM: PcAcid60 with a size exclusion limit of 60 Da. A 0.025 M sulfamic acid (amidosulfonic acid) solution was used as an electrolyte in the Electrodialysis process. Alternatively to the electrodialysis treatment a diafiltration process could be employed.

Example 7

Concentration and Activated Carbon Treatment

Some water was removed from the aqueous solution using a reversed osmosis filter and rotary evaporation at 45° C. to obtain a 25% (m/v) lacto-N-neotetraose solution. The resulting aqueous solution was then treated with activated carbon (Norit® SA2). 125 g activated carbon was employed for 1 L 25% (m/v) lacto-N-neotetraose solution.

Example 8

Sterile Filtration and Endotoxin Removal

Subsequently, the solution was subjected to sterile filtration by passing the solution through a 3 kDa filter (Pall Microza® ultrafiltration hollow fiber module SEP-2013, Pall Corporation, Dreieich, Germany). The sterile solution was then stored at RT until spray-drying.

Example 9

Spray-Drying of Lacto-N-Neotetraose.

The so obtained (example 8) sterile lacto-N-neotetraose were then spray-dried using a NUBILOSA LTC-GMP spray dryer (NUBILOSA, Konstanz, Germany). For the spray-drying of the lacto-N-neotetraose the solution was passed under pressure with 3.5 bar through the spray dryer nozzles set to 130° C. and flow was adjusted to maintaining an exhaust temperature between 67° C. to 69° C. Using these settings a spray-dried powder with less than 9% moisture could be obtained. The moisture contents were determined by Karl-Fischer titration.

Example 10

Separation of Lacto-N-Neotetraose and Para-Lacto-N-Neohexaose Using Simulated Moving Bed Chromatography in $Na^+$ Form A clear particle free solution containing lacto-N-neotetraose (20 g/l) as obtained from bacterial fermentation was electrodialysed to a conductivity of 0.5 mS/cm using a PC-Cell electrodialysis apparatus before using in SMB separation. In addition to lacto-N-neotetraose (66.23% of total carbohydrate content), this solution contained para-lacto-N-neohexaose (18.58% of total carbohydrate content) as the main by-product from the fermentation. For SMB chromatography with sodium as counter ion the lacto-N-neotetraose solution was concentrated to 200 g/l (20% w/v) under vacuum at 40° C. Alternatively, the lacto-N-neotetraose solution could be concentrated by using a nanofiltration membrane (XN45 from Trisep®).

For SMB chromatography a close loop SMB system equipped with 12 columns (Prosep® glas columns with the dimensions: 40 mm×740 mm (Lartek, Eppelheim, Germany) arranged in 4 zones was employed. Each glass column contained 760 g of Purolite® PCR833$H^+$ strong cationic ion exchanger resin. The cationic ion exchanger resin was washed with 50 Liter 200 mM NaCl to replace the $H^+$ ions by $Na^+$ ions. After equilibration the system was washed with water to remove the remaining salt.

The system was operated at 30° C. with the following parameter settings: flow rate zone I was set to 30.00 ml/min, flow rate of zone II was set to 21.60 ml/min, the flow rate of zone IV was set to 20.54 ml/min. Feed was kept at 1.5 ml/min and eluent flow was set to 4.46 ml/min with a switching time of 13.35 min. Distilled water was used as eluent.

Figure 4:
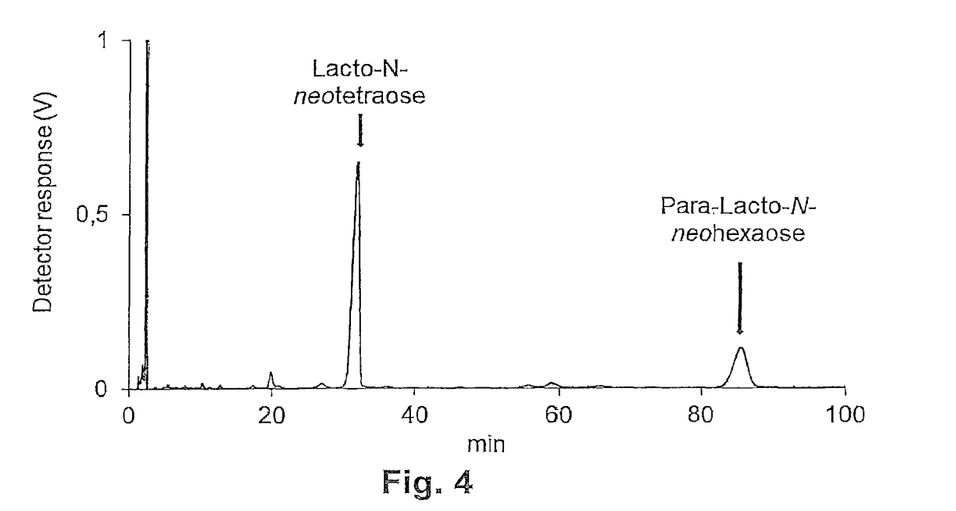
FIG. 4 displays the result of an HPLC analysis of an SMB Feed
Figure 5:
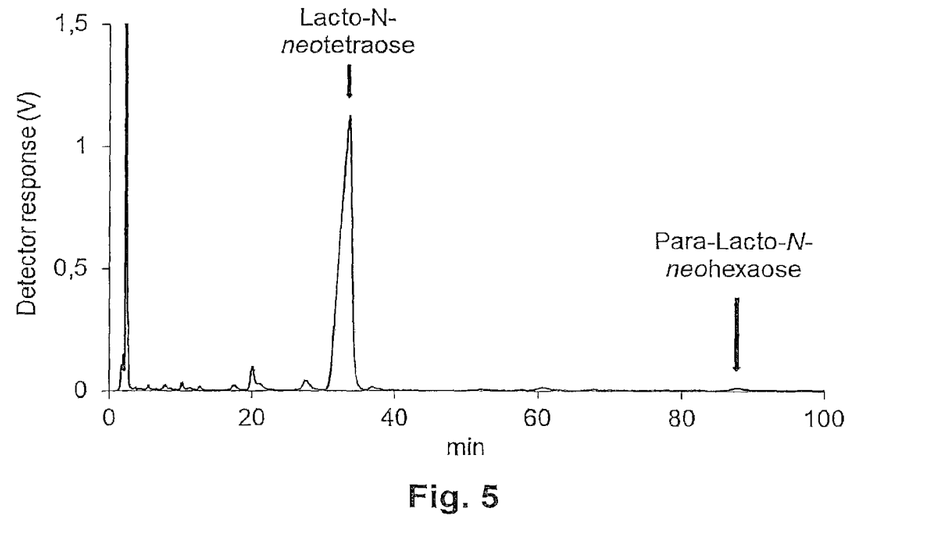
FIG. 5 displays the results of an HPLC analysis of an SMB extract.
Figure 6:
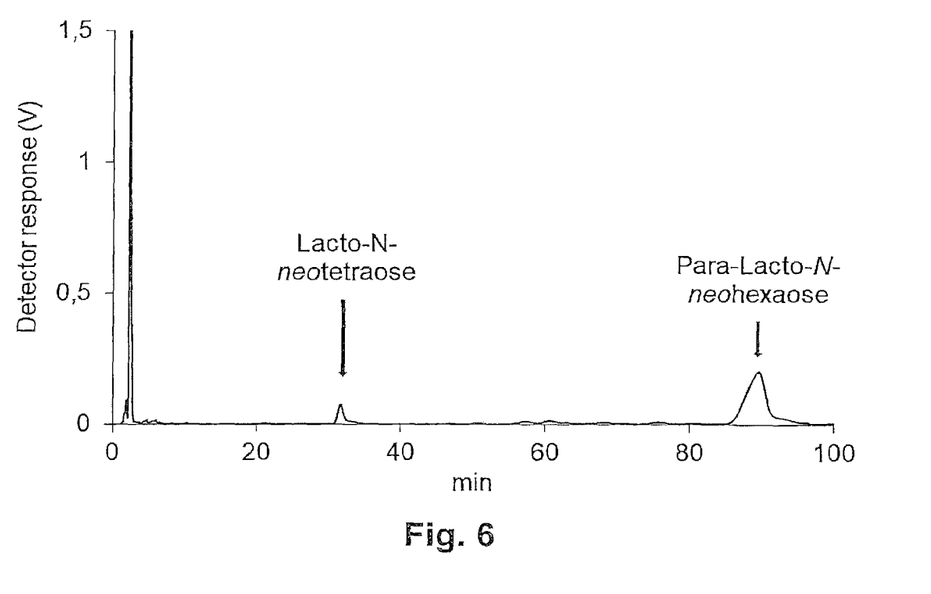
FIG. 6 displays the results of an HPLC analysis of an SMB raffinate.

Under these parameters the lacto-N-neotetraose and smaller neutral oligosaccharides like trioses (glycosylated or galactosylated lactose) were fractioned into the extract whereas the para-N-neohexose was eluted inside the raffinate. The purity of lacto-N-neotetraose was 87.3% instead of 66.23% at the SMB feed and the amount of para-lacto-N-neohexose was reduced to 1.08% (FIGS. 4 to 6).

Example 11

HPLC Analysis of Lacto-N-Neotetraose

The HPLC system, which was used for analysis of the LNnT-containing solutions consisted of a system controller SCL-10Avp, two pumps LC-10Avp, an oven CTO-10Avp, an autosampler SIL-HTA and a refractive index detector RID-10A. All modules were purchased from Shimadzu (Kyoto. Japan). In addition, a pre-column XBridge BEH Amide VanGd, 3.5 μm, 3.9×5 mm (Waters™, Eschborn, Germany) and a HPLC column XBridge BEH Amide, 3.5 μm, 4.6×250 mm (Waters, Eschborn, Germany) were used in this system. The solvent contained 71% acetonitile, 28.9% $H_2O$ and 0.1% $NH_4OH$. The flow rate was set to 1.4 mL/min. All HPLC measurements were performed isocratically with the solvent at 35° C. and the data were analysed qualitatively.

Example 12

LC-MS/MS Analysis of Lacto-N-Neotetraose

For LC-MS analysis to determine purity of LNnT with respect to the dry mass a Nexera X2 LC system (Shimadzu, Kyoto, Japan) was used, which included a LC-30AD pump, an autosampler SIL-30AC, a LCMS-8050 mass spectrometer (ESI-MS detector), a xBridge BEH Amide 3.5 μm, 50×2.1 mm column (Waters, Eschborn, Germany) and a xBridge BEH Amide 3.5 μm pre-column (Waters, Eschborn, Germany). The solvent contained 60% acetonitrile, 39.9% dd$H_2O$ and 0.1% $NH_4OH$ and the flow rate was set to 0.3 mL/min. All analyses were performed with the solvent isocratically at 35° C. Lacto-N-neotetraose was purchased from OligoTech (Crolles, France) and used as internal standard.

The invention claimed is:

1. A method for purification of lacto-N-neotetraose from other carbohydrates, wherein the method comprises subjecting an aqueous solution containing lacto-N- neotetraose (LNnT) to membrane filtration using a membrane having a molecular weight cut-off of about 300 to about 500 Dalton to remove carbohydrates having a molecular weight that is smaller than that of LNnT, followed by, subjecting the retentate of the membrane filtration to a continuous chromatography to remove carbohydrates having a molecular weight larger than that of LNnT from the aqueous solution after the membrane filtration.

2. The method according to claim 1, wherein the aqueous solution is obtained from a fermentation or enzymatic process for production of LNnT.

3. The method according to claim 1, wherein the aqueous solution is obtained from a fermentation by separating biomass from fermentation broth.

4. The method according to claim 3, wherein separating biomass from fermentation broth comprises a step of at least one ultrafiltration, of at least two ultrafiltrations, or of at least one of a first ultrafiltration using a membrane having a molecular weight cut-off of about 500 kDa and a second ultrafiltration using a membrane having a molecular weight cut-off of about 150 kDa.

5. The method according to claim 1, wherein the aqueous solution is further treated with a cation exchange resin and an anion exchange resin before subjecting aqueous solution which has been treated with ion exchange resins to membrane filtration.

6. The method according to claim 1, wherein the method further comprises dialysis or electrodialysis.

7. The method according to claim 1, wherein the purity of lacto-N- neotetraose in the aqueous solution is ≤70%, ≤60%, ≤50%, ≤40%, ≤30%, ≤20%, ≤10%, or ≤5% with respect to areas of peaks of a HPLC chromatogram prior to purification and/or the purified aqueous solution contains lacto-N-neotetraose at a purity of ≥80%, ≥85%, or ≥90% with respect to areas of peaks of a HPLC chromatogram after purification.

8. The method according to claim 3, wherein the method further comprises using at least one glycosidase for hydrolyzing one or more carbohydrates other than LNnT in the fermentation broth.

9. The method according to claim 3, wherein a second microorganism is added to the fermentation broth after fermentative production of LNnT, wherein said second microorganism expresses a β-galactosidase and/or a N-acetylhexosaminidase.

10. The method according to claim 9, wherein the β-galactosidase is encoded by *E. coli* lacZ, and/or the N-acetylhexosaminidase is encoded by bbhl of *B. bifidum*.

11. The method according to claim 5, wherein the cation exchange resin is in H+ form, and the anion exchange resin is in Cl- form.

* * * * *